(12) United States Patent
Klaus et al.

(10) Patent No.: US 6,403,810 B2
(45) Date of Patent: Jun. 11, 2002

(54) THIOPHENE DERIVATIVES

(75) Inventors: Michael Klaus, Weil am Rhein (DE); Jean-Marc Lapierre, Mountain View, CA (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/882,110

(22) Filed: Jun. 15, 2001

(30) Foreign Application Priority Data

Jul. 10, 2000 (EP) .............................................. 00114767

(51) Int. Cl.$^7$ ........................ A61K 31/38; A61K 31/19; C07D 333/38
(52) U.S. Cl. ........................ 549/71; 514/448; 514/438
(58) Field of Search ................................ 514/448, 438; 549/71, 29

(56) References Cited

U.S. PATENT DOCUMENTS

| | | | |
|---|---|---|---|
| 4,123,469 A | 10/1978 | Sprecker et al. | |
| 5,399,586 A | 3/1995 | Davies et al. | |
| 5,455,265 A | * 10/1995 | Chandraratna | ............... 514/448 |
| 5,475,022 A | * 12/1995 | Chandraratna | ............... 514/448 |
| 5,962,508 A | 10/1999 | Billoni et al. | |

OTHER PUBLICATIONS

References were mailed with prior office Action mailed on Aug. 31, 2001.*

Massaro, et al., Am. J. Physiol., 1996, 270, pp. L305–L310.

Massaro, et al., Nature Medicine (1997), vol. 3, pp. 675–677.

* cited by examiner

*Primary Examiner*—Joseph K. McKane
*Assistant Examiner*—Kamal Saeed
(74) *Attorney, Agent, or Firm*—George W. Johnston; Patricia S. Rocha-Tramaloni

(57) ABSTRACT

This invention relates to new retinoic acid receptor selective retinoid agonists, to pharmaceutical compositions containing such compounds, and to the use of such retinoic acid receptor agonists, particularly retinoic acid receptor γ (RARγ) selective agonists, for the treatment of emphysema and related pulmonary diseases.

14 Claims, No Drawings

THIOPHENE DERIVATIVES

SUMMARY OF THE INVENTION

The present invention relates to retinoic acid receptor ("RAR") selective retinoid agonists, pharmaceutical compositions containing such RAR agonists, to the use of such retinoic acid receptor agonists, particularly retinoic acid receptor γ (RARγ) selective agonists, for the treatment of emphysema and related pulmonary diseases. More specifically, the invention is directed to retinoic acid receptor agonists of formula I

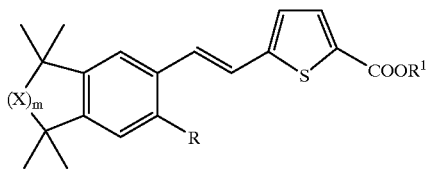

wherein X, R, $R^1$ and m are as defined below, and pharmaceutical compositions containing such compounds.

BACKGROUND OF THE INVENTION

Chronic obstructive pulmonary disease (COPD) is a major cause of morbidity and mortality, ranking third and fourth as the leading cause of death in the European Union and North America respectively. COPD is characterized by reduced maximum expiratory flow, which does not change over several months and which persists for 2 or more consecutive years. Patients with the most severe form of COPD generally present with a significant degree of emphysema. Emphysema is defined anatomically by permanent airspace enlargement distal to the terminal bronchioles. It is characterized by gradual loss of lung recoil, alveolar destruction, decreased alveolar surface area and gas exchange, leading to a reduced FEV1. These two features, impaired gas exchange and reduction in,expiratory flow, are characteristic physiological abnormalities from which patients with emphysema suffer. The main symptom of patients with severe emphysema is shortness of breath during minimal physical activity.

The most common cause of emphysema is cigarette smoking, although other potential environmental toxins may also contribute to the disease. These various insulting agents activate destructive processes in the lung, including release of active proteases and free radical oxidants in excess of protective mechanisms. The imbalance in protease/antiprotease levels leads to destruction of the elastin matrix, loss of elastic recoil, tissue damage and continuous decline in lung function. Avoiding injurious agents (i.e. cessation of smoking) slows the rate of damage. However, the damaged alveolar structures do not regenerate and to the extent lung function is lost, it is not regained.

Retinoic acid is a multifunctional modulator of cellular behavior, having the potential to alter both extracellular matrix metabolism and normal epithelial differentiation. In lung, retinoic acid has been shown to modulate various aspects of lung differentiation by interacting with specific retinoic acid receptors (RAR) that are selectively expressed temporally and spatially. Coordinated activation of RARβ and RARγ has been associated with lung branching and alveolization/septation. During alveolar septation, retinoic acid storage granules increase in the fibroblastic mesenchyme surrounding alveolar walls and RARγ expression in the lung peaks. Depletion of these retinyl-ester stores parallels the deposition of new elastin matrix and septation. It has been demonstrated that postnatal administration of retinoic acid increases the number of alveoli in rats. See Massaro et al., Am. J. Physiol., 1996, 270, L305–L3 10. Furthermore, the capacity of dexamethasone to prevent the expression of CRBP and RARβ mRNA and subsequent alveolar septation in developing rat lungs was abrogated by all-trans retinoic acid.

Recent studies have shown that all-trans retinoic acid can induce formation of new alveoli and return elastic recoil to near normal in animal models of emphysema (D. Massaro et al. Nature Medicine, 1997, 3, 675). However, the mechanism by which this occurs remains unclear.

Retinoids are a class of compounds structurally related to vitamin A, comprising natural and synthetic compounds. Several series of retinoids have been found clinically useful in the treatment of dermatological and oncological diseases. Retinoic acid and its other naturally occurring retinoid analogs (9-cis retinoic acid, all-trans 3,4-didehydro retinoic acid, 4-oxo retinoic acid and retinol) are pleiotropic regulatory compounds that modulate the structure and function of a wide variety of inflammatory, immune and structural cells. They are important regulators of epithelial cell proliferation, differentiation and morphogenesis in lungs. Retinoids exert their biological effects through a series of hormone nuclear receptors that are ligand inducible transcription factors belonging to the steroid/thyroid receptor superfamily. The retinoid receptors are classified into two families, the retinoic acid receptors (RARs) and the retinoid X receptors (RXRs), each consisting of three distinct subtypes (α,β, and γ). Each subtype of the RAR gene family encodes a variable number of isoforms arising from differential splicing of two primary RNA transcripts. All-trans retinoic acid is the physiological hormone for the retinoic acid receptors and binds with approximately equal affinity to all the three RAR subtypes, but does not bind to the RXR receptors for which 9-cis retinoic acid is the natural ligand.

In many non-pulmonary tissues, retinoids have antiinflammatory effects, alter the progression of epithelial cell differentiation, and inhibit stromal cell matrix production. These properties have led to the development of topical and systemic retinoid therapeutics for dermatological disorders such as psoriasis, acne, and hypertrophic cutaneous scars. Other applications include the control of acute promyelocytic leukemia, adeno- and squamous cell carcinoma, and hepatic fibrosis. A limitation in the therapeutic use of retinoids outside of cancer has stemmed from the relative toxicity observed with the naturally occurring retinoids, all-trans retinoic acid and 9-cis retinoic acid. These natural ligands are non-selective and therefore have pleiotropic effects throughout the body, which are often toxic. Recently various retinoids have been described that interact selectively or specifically with the RAR or RXR receptors or with specific subtypes (α,β,γ) within a class.

Thus, in addition to their use in the treatment of emphysema and other pulmonary diseases, the retinoids of the invention are useful in the therapy, amelioration, and prophylaxis of dermatological disorders which are accompanied by epithelial lesions, e.g. acne and psoriasis, light- and age-damaged skin; as well as for the promotion of wound healing, for example of incised wounds, such as surgical wounds, wounds caused by burns and other wounds caused by cutaneous trauma; and for the therapy and prophylaxis of malignant and premaligant epithelial lesions, tumors and precancerous changes of the mucous membrane in the mouth, tongue, larynx, oesophagus, bladder, cervix and colon.

DETAILED DESCRIPTION OF THE INVENTION

In one embodiment, the present invention is directed toward new RAR selective retinoid agonists of formula I

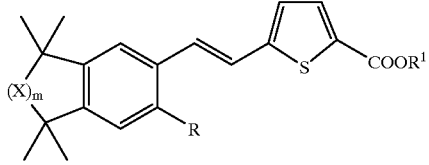

wherein

R is selected from the group consisting of hydrogen, alkyl, alkoxy, benzyl and phenethyl;

$R^1$ is hydrogen or alkyl;

X is $C(R^2R^3)$ and m is an integer 1, 2 or 3, or alternatively, X is oxygen, sulfur or NH and m is 1; and $R^2$, and $R^3$ are each independently selected from hydrogen and lower alkyl; and pharmaceutically acceptable salts of the carboxylic acids of compounds of formula I.

The term "alkyl" as used herein denotes straight chain or branched alkyl residues containing 1 to 10, preferably 1 to 7, carbon atoms, such as methyl, ethyl, isobutyl, pentyl, amyl, 3-pentyl, hexyl, heptyl and the like. The term "lower alkyl" as used herein denotes alkyl residues as defined above, but having 1 to 5 carbon atoms.

As used herein, the term "alkoxy" refers to a straight or branched chain hydrocarbonoxy group wherein the "alkyl" portion is an alkyl group as defined above. Examples include methoxy, ethoxy, n-propyloxy and the like.

The term "pharmaceutically acceptable" such as pharmaceutically acceptable carrier, excipient, salt, etc., means pharmacologically acceptable and substantially non-toxic to the subject to which the particular compound is administered.

The compounds of formula I wherein $R^1$ is hydrogen form salts with pharmaceutically acceptable bases such as alkali salts, e.g. Na- and K-salts, or ammonium or substituted ammonium salts such as trimethylammonium salts, all of which are contemplated in this invention.

Preferred compounds of formula I are compounds wherein X is $C(R^2R^3)$ and m is 2. Particularly preferred compounds are those wherein $R^1$, $R^2$ and $R^3$ are hydrogen and R is alkyl selected from pentyl and hexyl, for example, the following compounds:

(E)-5-[2-(3-hexyl-5,5,8,8-tetramethyl-5,6,7,8-tetrahydro-naphthalen-2-yl)-vinyl]-thiophene-2-carboxylic acid; and (E)-5-[2-(3-pentyl-5,5,8,8-tetramethyl-5,6,7,8-tetrahydro-naphthalen-2-yl)-vinyl]-thiophene-2-carboxylic acid.

The compounds of formula I can be prepared according to synthetic scheme 1 below. The starting material 5,5,8,8-tetramethyl-5,6,7,8-tetrahydronaphthalene, compound 1, can be prepared in accordance to the teachings of U.S. Pat. No. 4,123,469. compound 1 is subjected to a Friedels-Kraft acylation, followed by a reduction of the carbonyl under $H_2$ atmosphere in presence of Pd/C, giving the intermediate 2 in high yield.

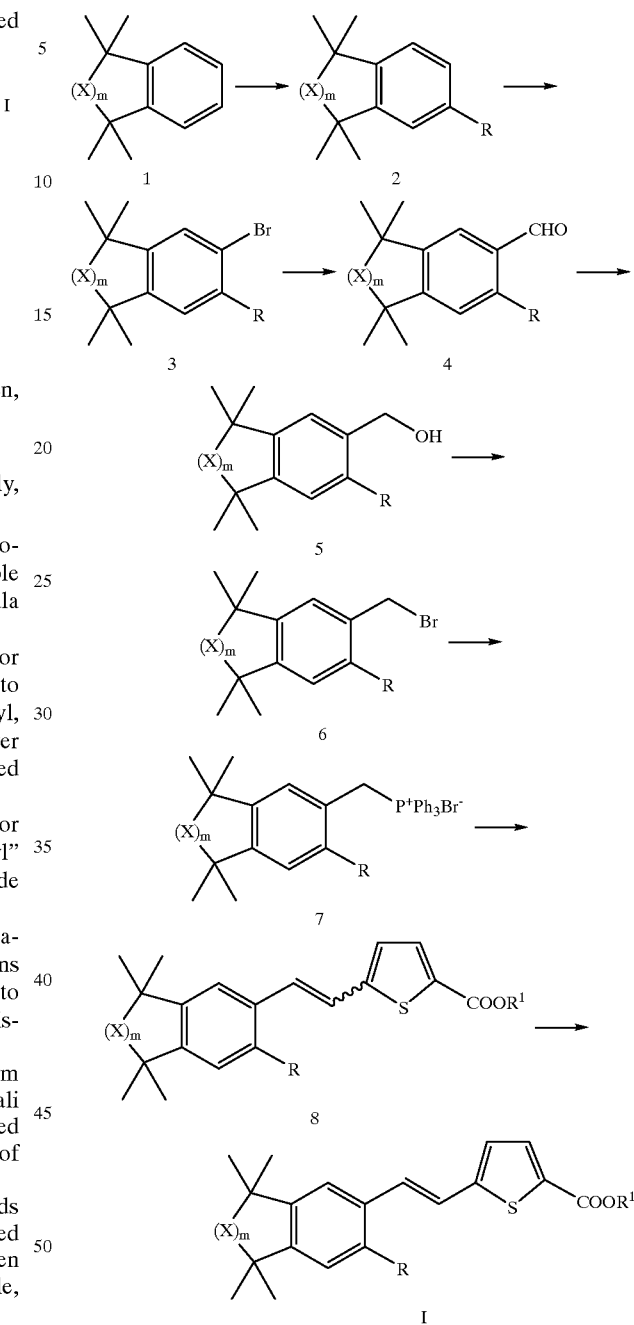

wherein X, R and $R^1$ and m are as defined above.

Bromination of compound 2 under $Br_2$/Fe provided compound 3, which when treated with BuLi and of N,N-dimethylformamide (DMF), yields the aldehyde compound 4. Reduction of compound 4 in the presence of $BH_3$.THF, at 0° C., yields alcohol 5. Bromination of compound 5 at the benzylic position ($CBr_4$/$Ph_3P$) yields compound 6. The phosphonium salt 7, is then obtained by treatment of compound 6 with $Ph_3P$ in refluxing toluene. A Wittig reaction of 5-formyl-2-thiophene carboxylic methyl ester with the phosphonium salt compound 7 yields olefin compound 8 in good yield with a cis/trans ratio 1:14.

Isomer separation can be achieved by using a medium pressure liquid chromatography (MPLC). The desired ester of E configuration can then be hydrolysed under standard conditions to the corresponding acid, i.e. the compound of formula I, wherein R¹ is hydrogen.

Alternatively, compounds of formula I may be prepared pursuant to Scheme 2 below.

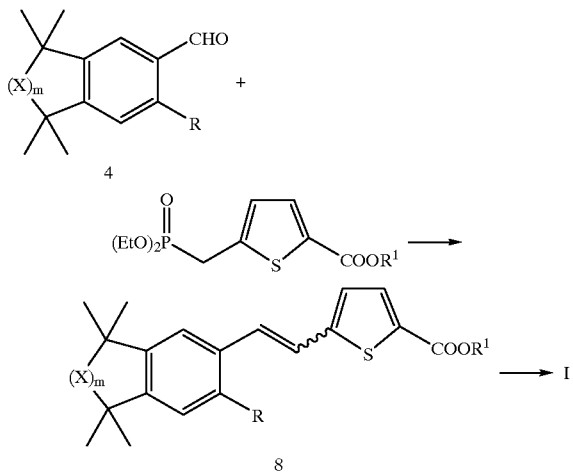

Scheme 2

The aldehyde 4 is reacted with the appropriate phosphonate in a Wittig-Horner reaction. The olefin thus obtained (compound 8) is almost exclusively of E geometry. Hydrolysis under standard conditions known in the art and recrystallization provides the compounds of formula I wherein $R^1$ is hydrogen, and with exclusive E-symmetry double bond.

Compounds of formula I wherein X is oxygen, sulfur or NH and m is 1 can be prepared by analogy to the method described above, starting from the corresponding 2,3-dihydro-1H-isoindole, 1,3-dihydro-benzo[c]thiophen and 1,3-dihydro-benzofuran, respectively (Tetrahedron, 1992, 48, 10569; Aust. J. Chem., 1983, 36, 397).

This invention is also directed to a method for treating or controlling emphysema and associated pulmonary diseases by administering to a patient in need of such treatment a therapeutically effective amount of a RAR selective agonist of formula I. Systemic administration of compounds of formula I is the preferred mode of delivery.

As used herein, a "therapeutically effective amount" means an amount of a compound that, when administered to a mammal, particularly a human patient, for treating, preventing, controlling, or ameliorating a disease is sufficient to effect such treatment, prevention, control, or amelioration of the disease. The "therapeutically effective amount" will vary depending on the compound, the disease and its severity, and the age, weight, etc., of the mammal to be treated. A typical dose of a compound of formula I is between about 1 and about 100 µg/kg body weight per day, preferably from about 5 to about 50 µg/kg body weight per day.

The RARγ agonist selectivity of a compound can be determined by routine ligand binding assays known to those skilled in the art, for example, the assays described in C. Apfel etal. *Proc. Nat. Sci. Acad. (USA)*, 89:7129–7133 (1992); M. Teng et al., *J. Med. Chem.* 40:2445–2451 (1997); and PCT Publication WO 96/30009.

Treatment with RAR agonists, particularly RARγ selective agonists, is useful to promote repair of alveolar matrix and septation. Thus, the RAR agonists taught in this invention are useful for promoting the repair of damaged alveoli and septation of new alveoli, particularly for the treatment emphysema.

The particular dosage of a RAR selective agonist of formula I required to treat lung emphysema is dependant on the severity of the condition. This dosage may be delivered in a conventional pharmaceutical composition by a single administration, by multiple applications, or via controlled release, as needed to achieve the most effective results. Dosing will continue for as long as is medically indicated, which depending on the severity of the disease may range from a few weeks to several months.

This invention is also directed to pharmaceutical compositions containing compounds of formula I and a pharmaceutically acceptable carrier, excipient and/or diluent. Typical pharmaceutically acceptable compositions, of an RAR agonist of formula I include the salts of such compounds and a pharmaceutically acceptable carrier. In the context of the present invention, "pharmaceutically acceptable salts" include any chemically suitable salt known in the art of retinoid agonists as applicable for administration to human patients. Examples of conventional salts known in the art include the alkali metal salts such as sodium and potassium salts, the alkaline earth metal salts such as calcium and magnesium salts, and ammonium and alkyl ammonium salts.

Representative delivery regimens include oral, parenteral (including subcutaneous, intramuscular and intravenous), rectal, buccal (including sublingual), transdermal, pulmonary and intranasal. One method of pulmonary administration involves aerosolization of a solution of an RAR agonist. Aerosolized compositions may include the compound packaged in reverse micelles or liposomes. Typical pulmonary and respiratory delivery systems are described in U.S. Pat. Nos. 5,607,915, 5,238,683, 5,292,499, and 5,364,615.

The treatment methods of this invention also include systemic administration of RAR agonists in simultaneous or sequential combination with one or more additional active ingredients.

The RAR agonists of the invention typically will be administered as pharmaceutical compositions in admixture with a pharmaceutically acceptable carrier. As mentioned above, such compositions may be prepared for parenteral (subcutaneous, intramuscular or intravenous) administration, particularly in the form of liquid solutions or suspensions; for oral or buccal administration, particularly in the form of tablets or capsules; for intranasal administration, particularly in the form of powders, nasal drops or aerosols; and for rectal or transdermal administration. Any conventional carrier material can be employed. Suitable pharmaceutically acceptable carriers include organic or inorganic carrier materials, such as water, gelatin, gum arabic, lactose, starch, magnesium stearate, talc, polyalkylene glycols, petroleum jelly and the like.

Liquid formulations for parenteral administration may contain as excipients sterile water or saline, alkylene glycols such as propylene glycol, polyalkylene glycols such as polyethylene glycol, oils of vegetable origin, hydrogenated naphthalenes and the like. They may employ slightly acidic buffers in pH ranges of about 4 to about 6. Suitable buffers include acetate, ascorbate and citrate at concentrations ranging from about 5 mM to about 50 mM. For oral administration, the formulation can be enhanced by the addition of bile salts or acylcarnitines.

Formulations for nasal administration may be solid and may contain excipients, for example, lactose or dextran, or may be aqueous or oily solutions for use in the form of nasal drops or metered spray. Particular nasal formulations include dry powders suitable for conventional dry powder inhalers (DPI's), liquid solutions or suspensions suitable for nebulization and propellant formulations suitable for use in metered dose inhalers (MDI's). For buccal administration typical excipients include sugars, calcium stearate, magnesium stearate, pregelatinated starch, and the like.

In formulations for nasal administration, the absorption across the nasal mucous membrane may be enhanced by inclusion of surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Solid forms for oral administration include tablets, hard and soft gelatin capsules, pills, sachets, powders, granules and the like. Each tablet, pill or sachet may contain from about 1 to about 50 mg, preferably from 5 to about 10 mg of RAR agonist. Preferred solid oral dosage forms include tablets, two-piece hard shell capsules and soft elastic gelatin (SEG) capsules. SEG capsules are of particular interest because they provide distinct advantages over the other two forms (see Seager, H., "Soft gelatin capsules: a solution to many tableting problems"; Pharmaceutical Technology, 9, (1985). Some of the advantages of using SEG capsules are: a) dose-content uniformity is optimized in SEG capsules because the drug is dissolved or dispersed in a liquid that can be dosed into the capsules accurately b) drugs formulated as SEG capsules show good bioavailability because the drug is dissolved, solubilized or dispersed in an aqueous-miscible or oily liquid and therefore when released in the body the solutions dissolve or are emulsified to produce drug dispersions of high surface area and c) degradation of drugs that are sensitive to oxidation during long-term storage is prevented because of the dry shell.

Delivery of the compounds of the present invention to a patient over prolonged periods of time, for example, for periods of from one week to one year, may be accomplished by a single administration of a controlled release system containing sufficient active ingredient of formula I for the desired release period. Various controlled release systems, such as monolithic or reservoir type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

The following are representative pharmaceutical formulations for using RAR selective agonists as described herein for promoting elastin mediated matrix repair and alveolar septation.

Tablet Formulation

The following ingredients are mixed thoroughly and pressed into single scored tablets.

| Quantity per Ingredient | tablet, mg |
|---|---|
| RAR agonist | 10 |
| cornstarch | 50 |
| croscarmellose sodium | 25 |
| lactose | 120 |
| magnesium stearate | 5 |

Capsule Formulation

The following ingredients are mixed thoroughly and loaded into a hard-shell gelatin capsule.

| Ingredient | Quantity per capsule, mg |
|---|---|
| RAR agonist | 5 |
| lactose, spray-dried | 148 |
| magnesium stearate | 2 |

Suspension Formulation

The following ingredients are mixed to form a suspension for oral administration.

| Ingredient | Amount |
|---|---|
| RAR agonist | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
|---|---|
| RAR agonist | 0.2 g |
| sodium acetate buffer solution, 0.4M | 2.0 ml |
| HCl (1N) or NaOH (1N) | q.s. to suitable pH |
| water (distilled, sterile) | q.s. to 20 ml |

Nasal Formulation

The following ingredients are mixed to form a suspension for nasal administration.

| Ingredient | Amount |
|---|---|
| RAR agonist | 20 mg/ml |
| citric acid | 0.2 mg/ml |
| sodium citrate | 2.6 mg/ml |
| benzalkonium chloride | 0.2 mg/ml |
| sorbitol | 35 mg/ml |
| sodium taurocholate or glycocholate | 10 mg/ml |

The following examples are illustrative of the present invention, but are not intended to limit the scope of the invention.

EXAMPLE 1

1.1 Prepration of 1-(5,5,8,8-Tetramethyl-5,6,7,8-tetrahydro-naphthalen-2-1-hexanone A solution of 8.6 ml of hexanoyl chloride in 35 ml of methylene chloride was treated portionwise, at 0° C., with 7.9 g of aluminium chloride. The mixture was stirred at 0°

C. for 30 min. then a solution of 10.0 g of 5,5,8,8-tetramethyl-5,6,7,8-tetrahydronaphthalene in 12 ml of methylene chloride was added dropwise to the cooled reaction mixture. The reaction mixture was kept at 0° C. for four hours, then poured onto 100 ml ice/water. The mixture was extracted with 3 portions of 200 ml of methylene chloride. The combined organic extracts were washed with one portion of 200 ml of saturated aqueous sodium bicarbonate solution, one portion of 200 ml water and one portion of 200 ml of saturated aqueous sodium chloride solution. The organic phase was dried over $MgSO_4$ and concentrated in vacuo, giving an orange oil. The crude product was distilled under vacuum, yielding 13.8 g of a pale yellow oil. B.p. 138–140° C. at 0.1 bar.

In analogy to example 1.1, the following compound was prepared using pentanoyl chloride:

1-(5,5,8,8-tetramethyl-5,6,7,8-tetrahydronaphthalen-2-yl)- 1-pentanone.

1H NMR ($CDCl_3$): 7.93 (d, J=3.0 Hz, 1H), 7.70 (dd, J=9.0, 3.0 Hz, 1H), 7.38 (d, J=9.0 Hz, 1H), 2.91 (t, J=7.2 Hz, 2H), 1.65–1.80 (m, 2H), 1.70 (s, 4H), 1.20–1.45 (m, 4H), 1.31 (s, 6H), 1.29 (s, 6H), 0.90 (t, J=7.4 Hz, 3H).

EXAMPLE 2

2.1 Preparation of 2-Hexyl-5,5,8,8-tetramethyl-5,6,7,8-tetrahydronaphthalene

A solution of 13.8 g of 1-(5,5,8,8-tetramethyl-5,6,7,8-tetrahydro-naphthalen-2-yl)-1-hexanone (from Example 1.1) in 200 ml ethanol abs., containing 2 g of palladium on carbon 10% and 3 drops of HCl 25%, was subjected to $H_2$ atmosphere for 3 hours (until consumption of theoretical amount $H_2$ is reached and thin layer chromatography showed no more starting material was present). The mixture was filtered and concentrated in vacuo. The residue was diluted in 200 ml ether, dried over $MgSO_4$, filtered and concentrated in vacuo, giving a yellow oil. The crude product was distilled under vacuum (T=120° C. at 0.08 bar), yielding a pale yellow oil (12.1 g). B.p. 120° C. at 0.08 bar.

In analogy to example 2.1, using the compound from example 1.2, the following product was prepared:

2-pentyl-5,5,8,8-tetramethyl-5,6,7,8-tetrahydronaphthalene.

1H NMR ($CDCL_3$): 7.20 (d, J=8.0 Hz, 1H), 7.10 (d, J=2.4 Hz, 1H), 6.94 (dd, J=2.4 Hz, 1H), 2.54 (t, J=7.8 Hz, 2H), 1.67 (s, 4H), 1.50–1.70 (m, 2H), 1.20–1.45 (m, 4H), 1.27 (s, 6H), 1.26 (s, 6H), 0.89 (t, J=6.8 Hz, 3H).

EXAMPLE 3

3.1 Preparation of 3-Bromo-2-hexyl-5,5,8,8-tetramethyl-5,6,7,8-tetrahydronaphthalene A solution of 2-hexyl-5,5,8,8-tetramethyl-5,6,7,8-tetrahydro-naphthalene (from Example 2.1, 12.1 g) in 80 ml of carbon tetrachloride, containing 327 mg of pulverised iron powder, was cooled to 0° C. and treated dropwise with a solution of 7.84 g of $Br_2$ in 8 ml of carbon tetrachloride. The mixture was stirred at 0° C. for 4 hours. The reaction mixture was filtered and then poured into 200 ml ice/water. Extraction of the biphasic mixture with 3 portions of 100 ml of methylene chloride was followed by a washing of the combined organic extracts with 100 ml of saturated aqueous sodium bicarbonate solution and 100 ml water. The organic phase was dried over $MgSO_4$ and concentrated in vacuo, giving a yellow oil. The crude product was distilled under vacuum, yielding 14 g of a pale yellow oil. B.p. 148° C. at 0.09 bar.

In analogy to example 3.1, using the compound from example 2.2, the following product was obtained:

3-bromo-2-pentyl-5,5,8,8-tetramethyl-5,6,7,8-naphthalene.

1H NMR ($CDCl_3$): 7.40 (s, 1H), 7.10 (s, 1H), 2.65 (t, J=8.3 Hz, 2H), 1.50–1.70 (m, 2H), 1.65 (s, 4H), 1.20–1.50 (m, 4H), 1.25 (s, 12H), 0.91 (m, 3H).

EXAMPLE 4

4.1 Preparation of 3-Hexyl-5,5,8,8-tetramethyl-5,6,7,8-tetrahvdronaphth-2-aldehyde A solution of 5.43 g of 3-bromo-2-hexyl-5,5,8,8-tetramethyl-5,6,7,8-tetrahydronaphthalene in 110 ml of THF was cooled to −78° C. with an acetone/dry ice bath and treated dropwise with 14.5 ml of butyllithium 1.6M in hexane (1.5 eq.). The mixture was kept at −78° C. for 1 hour. DMF (2.4 ml) was added at −78° C. The reaction mixture was stirred at −78° C. for 15 min. then was allowed to warm to room temperature for 2 hours. The mixture was quenched with water (100 ml) and the pH was adjusted to 2 with hydrochloric acid 25%. The mixture was extracted with 3 portions of 100 ml of ether. The combined organic extracts were washed with water (100 ml) and saturated aqueous sodium chloride solution (100 ml). The organic phase was dried over $MgSO_4$, filtered and concentrated in vacuo, giving a yellow oil. The product was purified by flash chromatography ($SiO_2$, hexane then 5% ethyl acetate/hexane) yielding 4.41 g of a pale yellow oil.

1H NMR ($CDCl_3$): 10.19 (s, 1H), 7.75 (s, 1H), 7.14 (s, 1H), 2.94 (t, J=8.3 Hz, 2H), 1.68 (s, 4H), 1.50–1.70 (m, 2H), 1.20–1.45 (m, 6H), 1.29 (s, 12H), 0.87 (m,3H).

In analogy to example 4.1, using the compound from example 3.2, the following product was obtained:

3-pentyl-5,5,8,8-tetramethyl-5,6,7,8-tetrahydronaphth-2-aldehyde.

1H NMR ($CDCl_3$): 10.20 (s, 1H), 7.76 (s, 1H), 7.16 (s, 1H), 2.95 (t, J=8.2 Hz, 2H), 1.69 (s, 4H), 1.50–1.70 (m, 2H), 1.25–1.50 (m, 4H), 1.30 (s, 6H), 1.29 (s, 6H), 0.90 (t, J=6.1 Hz, 3H).

EXAMPLE 5

5.1 Preparation of (3-Hexyl-5,5,8,8-tetramethyl-5,6,7,8-tetrahydronaphth-2-yl)-methanol A solution of 4.14 g of 3-hexyl-5,5,8,8-tetramethyl-5,6,7,8-tetrahydronaphth-2-aldehyde (from Example 4.1) in 20 ml of THF was cooled to 0° C. and treated with 13.8 ml of borane-THF complex sol. 1M in THF (3 H eq.). The mixture was stirred at room temperature for 90 min., then cooled back at 0° C. and quenched carefully by the addition of 30 ml of hydrochloric acid 3N. The mixture was stirred at room temperature for 30 min., then was extracted with 3 portions of 100 ml ether. The combined extracts were washed with water (100 ml) and a saturated aqueous sodium chloride solution (100 ml). The organic phase was dried over $MgSO_4$, filtered and concentrated in vacuo, giving a pale yellow oil. Flash chromatography ($SiO_2$, 10% ethyl acetate/hexane) afforded 3.80 g of the title compound as a colourless oil. 1 H NMR ($CDCl_3$): 7.27 (s, 1H), 7.11 (s, 1H), 4.67 (d, J=5.7 Hz, 2H), 2.59 (t, J=8.3 Hz, 2H), 1.67 (s, 4H), 1.50–1.65 (m, 2H), 1.20–1.45 (m,6H), 1.28 (s, 6H), 1.27 (s, 6H), 0.89 (t, J=6.6 Hz, 3H).

EXAMPLE 6

6.1 Preparation of 2-Bromomethyl-3-hexyl-5,5,8,8-tetramethyl-5,6,7,8-tetrahydronaphthalene A solution of 3.43 g of (3-hexyl-5,5,8,8-tetramethyl)-5,6, 7,8-tetrahydro-naphthalen-2-yl)-methanol (from Example 5.1) in 100 ml THF was treated with 3.72 g of triphenylphosphine and 4.70 g of tetrabromomethane. The mixture was stirred at room temperature for 3 hours. The reaction mixture was diluted with water (100 ml) and extracted with 3 portions of 100 ml of ethyl acetate. The combined organic phases were dried ($MgSO_4$), filtered and concentrated in vacuo. The resulting yellow oil was triturated in pentane (100 ml) and the solid was removed. The filtrate was concentrated in vacuo, giving a pale yellow oil. Flash chromatography ($SiO_2$, hexane) gave 2.58 g of the title product as a colourless oil.

1H NMR ($CDCl_3$): 7.23 (s, 1H), 7.09 (s, 1H), 4.53 (s, 2H), 2.66 (t, J=7.9 Hz, 2H), 1.66 (s, 4H), 1.60–1.70 (m, 2H), 1.25–1.45 (m, 6H), 1.26 (s, 12 H), 0.90 (t, J=7.2 Hz, 3H).

EXAMPLE 7

7.1 Preparation of (3-Hexyl-5,5,8,8-tetramethyl-5,6,7,8-tetrahydronaphthalen-2-yl)-methyl Triphenylphosphonium Bromide A solution of 2.58 g of 2-bromomethyl-3-hexyl-5,5,8,8-tetramethyl-5,6,7,8-tetrahydro-naphthalene (from Example 6) and 1.94 g of triphenylphosphine in 50 ml of toluene was heated to reflux (oil bath at 115° C.) for 3 hours. The mixture was cooled to −5° C. for 1 hour and the white solid was filtered off. Concentration in vacuo of the filtrate gave a pale yellow residue, which was crystallized from toluene. The combined white solids were dried, giving 4.0 g of the title product. 1H NMR ($CDCL_3$): 7.78 (m, 3H), 7.50–7.75 (m, 12 H), 6.95 (s, 1H), 6.90 (s, 1H), 5.14 (d, J=15 Hz, 2H), 1.76 (t, J=7.8 Hz, 2 H), 1.50–1.70 (m, 4 H), 1.22 (s, 6 H), 1.30–1.05 (m, 8 H), 0.85 (t, J=6.8 Hz, 3 H), 0.81 (s, 6 H).

EXAMPLE 8

8.1 Preparation of Methyl (E)-5-[2-(3-hexyl-5,5,8,8-tetramethyl-5,6,7,8-tetrahydronaphtalen-2-yl)-vinyl]-thiophene -2-carboxylate A suspension of 1.917 g of (3-hexyl-5,5,8,8-tetramethyl-5,6,7,8-tetrahydro-naphthalen-2-yl)-methyl triphenylphosphonium bromide (From Example 7.1) in 40 ml THF was cooled to −78° C. and treated with 1.91 ml of butyllithium 1.6 M in hexane. The mixture was allowed to warm to room temperature for 30 min. then was cooled back to −78° C. A solution of 495 mg of methyl 5-formylthiophene-2-carboxylate in 10 ml THF was added. The mixture was kept at −78° C. for 30 min. then was allowed to warm to room temperature for 30 min. The reaction mixture was diluted with 50 ml of a saturated ammonium chloride solution and extracted with 3 portions of 50 ml of ethyl acetate. The combined organic extracts were dried ($MgSO_4$), filtered and concentrated in vacuo, giving a yellow solid. Flash chromatography ($SiO_2$, 3% ethyl acetate/hexane) gave 1.2 g of a mixture (E/Z) of the desired product. Chromatography on a medium pressure liquid chromatography system (3% ethyl acetate/hexane) provided 1.12 g of the title product without trace of the Z isomer. 1H NMR ($CDCl_3$): 7.69 (d, J=4.5 Hz, 1H), 7.48 (s, 1H), 7.30 (d, J=15.6 Hz, 1H), 7.09 (s, 1H), 7.05 (d, J=4.9 Hz, 1H), 7.04 (d, J=15.6 Hz, 1H), 3.89 (s, 3H), 2.67 (t, J=8.3 Hz, 2H), 1.68 (s, 4H), 1.2–1.5 (m, 8H), 1.32 (s, 6H), 1.28 (s, 6H), 0.90 (t, J=7.0 Hz, 3H).

8.2 Alternative Method of Preparing Ethyl (E)-5-[2-(3-pentyl-5,5,8,8-tetramethyl-5,6,7,8-tetrahydronaphthalen-2-yl) -vinyl]-thiophene-2-carboxylate A solution of 1.027 g of diethyl (5-ethoxycarbonylthiophen-2-yl)-methyl phosphonate in 15 ml THF was cooled at −25° C. and treated with 3.35 ml of lithium hexamethyldisilazide 1.0 M in hexane. The mixture was kept at −25° C. for 15 min. then a solution of 733 mg of 3-pentyl-5,5,8,8-tetramethyl-5,6,7,8-tetrahydronaphth-2-aldehyde in 7 ml THF was added. The mixture was allowed to warm to room temperature for 2 hours. The reaction mixture was diluted with 15 ml water and 15 ml of a aqueous saturated ammonium chloride solution. The mixture was extracted with 3 portions of 15 ml of ethyl acetate. Combined organic extracts were dried ($MgSO_4$), filtered and concentrated in vacuo, giving a yellow oil.

1H NMR ($CDCl_3$): 7.66 (d, J=4.5 Hz,1H),7.47 (s, 1H), 7.28 (d, J=16.5 Hz,1H,) 7.08 (s, 1H), 7.05 (d, J=4.5 Hz, 1H), 7.04 (d, J=16.5 Hz, 1H) 4.37 (q, J=7.0 Hz, 2H), 2.67 (t, J=7.8 Hz, 2H), 1.68 (s, 4H), 1.2–1.5 (m, 6H), 1.38 (t, J=7.0 Hz, 3H), 1.31 (s, 6H), 1.28 (s, 6H), 0.91 (t, J=7.2 Hz, 3H).

EXAMPLE 9

9.1 Preparation of (E)-5-[2-(3-Hexyl-5,5,8,8-tetramethyl-5,6,7,8-tetrahydro-naphthalen-2-yl)-vinyl]-thiophene-2-carboxylic Acid A solution of 1.084 g of methyl (E)-5-[2-(3-hexyl-5,5,8,8-tetramethyl-5,6,7,8-tetrahydronaphthalen-2-yl)-vinyl]-thiophene-2-carboxylate (from Example 8.1) in 15 ml ethanol was treated with a solution of 2.77 g KOH in 8 ml H20, followed by the addition of 7 ml THF. The mixture was stirred at 45° C. for 2.5 hours. The reaction mixture was diluted with 40 ml water and acidified to pH 2 with HCl 25%. The mixture was extracted with 4 portions of 50 ml of ethyl acetate. The combined extracts were washed with 50 ml water and 50 ml of aqueous saturated sodium chloride solution. Drying ($MgSO_4$), filtration and concentration in vacuo gave a pale yellow solid. Trituration in pentane and filtration afforded 952 mg of the title product as a pale yellow solid. M.p. 164–165° C.

In analogy to example 9.1, the following acid was also prepared. 9.2 (E)-5-[2-(3-pentyl-5,5,8,8-tetramethyl-5,6,7,8-tetrahydro-naphthalen-2-yl)-vinyl]thiophene-2-carboxylic acid. M.p. 176–177° C.

EXAMPLE 10

Effects of RAR Selective Retinoids on Repair of Alveoli in Elastase-induced Emphysema A RAR selective agonist according to the invention was evaluated for its effects on alveolar repair in a rat model for rat elastase-induced emphysema in accordance to D. Massaro et al. *Nature Medicine* 1997, 3, 675. Animals were divided into treatment groups of approximately eight. Lung inflammation and alveolar damage was induced in male Sprague Dawley rats by a single instillation of pancreatic elastase(porcine derived, Calbiochem) 2 U/gram body mass. Three weeks post injury, all-trans retinoic acid or RAR agonist test compound was dissolved in dimethyl-sulfoxide (20 mg/ml) and stored at −20 C. Fresh working stocks were prepared daily by dilution in PBS to a final concentration of 2mg/ml. Animals were dosed once daily with the retinoid by intraperitoneal injection or orally, starting 21 days post injury. Control groups were challenged with elastase and 21 days later treated with Vehicle (DMSO/PBS) for 14 days. Animals were sacrificed 24 hours after the last dose by exsanguination under deep anesthesia.

The lungs were inflated with 10% neutral buffered formalin by intratracheal instillation at a constant rate (1 ml/gram body mass/min). The lung was excised and immersed in fixative for 24 hours prior to processing. Standard methods were used to prepare 5 μm paraffin sections. Sections were stained with Hematoxylin and Eosin (H%E). Computerized Morphometric analysis was performed to determine the average alveolar size and alveolar number. The results of this test are reported in Table 1 below.

TABLE 1

Data is given for (E)-5-[2-(3-hexyl-5,5,8,8-tetramethyl-5,6,7,8-tetrahydronaphthalen-2-yl)-vinyl]-thiophene-2-carboxylic acid (the compound of Example 9):

| Dose [mg/kg] | Route of Administration | % repair area |
|---|---|---|
| 0.1 | oral | 42 |
| 0.01 | oral | 18 |
| 0.001 | oral | 42 |
| 0.0001 | oral | 38 |

The foregoing invention has been described in some detail by way of illustration and example, for the purposes of clarity and understanding. It will be obvious to one of ordinary skill in the art that changes and modifications may be practiced within the scope of the appended claims. Therefore, it is to be understood that the above description is intended to be illustrative and not restrictive. The scope of the invention should, therefore, be determined with reference to the following appended claims, along with the full scope of equivalents to which such claims are entitled.

The patents, patent publications and articles cited in this application are hereby incorporated by reference, in their entirety and for the extent required, to the same extent as if each individual document were individually reproduced herein.

What is claimed is:

1. A compound of formula I

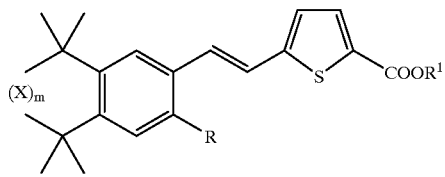

wherein

R is selected from the group consisting of hydrogen, alkyl, alkoxy, benzyl and phenethyl;

$R^1$ is hydrogen or alkyl;

X is $C(R^2R^3)$ and m is an integer 1, 2 or 3, or alternatively, X is oxygen, sulfur or NH and m is 1;

$R^2$, and $R^3$ are each independently selected from hydrogen and lower alkyl; and pharmaceutically acceptable salts of such compounds.

2. The compound of claim 1, wherein X is $CR^2R^3$ and m is 2.

3. The compound of claim 2, wherein $R^1$, $R^2$ and $R^3$ are hydrogen.

4. The compound of claim 3, wherein R is alkyl.

5. The compound of claim 4, wherein R is pentyl or hexyl.

6. The compound (E)-5-[2-(3-hexyl-5,5,8,8-tetramethyl-5,6,7,8-tetrahydro-naphthalen-2-yl)-vinyl]-thiophene-2-carboxylic acid.

7. The compound (E)-5-[2-(3-pentyl-5,5,8,8-tetramethyl-5,6,7,8-tetrahydro-naphthalen-2-yl)-vinyl]-thiophene-2-carboxylic acid.

8. The salt of a compound of claim 1, wherein $R^1$ is hydrogen, which salt is formed from a base selected from alkali, ammonium, and substituted ammonium.

9. A pharmaceutical composition comprising as an active ingredient an effective amount of a compound of claim 1 and a pharmaceutically acceptable carrier or excipient.

10. A pharmaceutical composition, comprising as an active ingredient an effective amount of a compound of claim 6 and a pharmaceutically acceptable carrier or excipient.

11. A pharmaceutical composition comprising as an active ingredient an effective amount of a compound of claim 7 and a pharmaceutically acceptable carrier or excipient.

12. The pharmaceutical composition of claim 9 which is suitable for systemic administration.

13. The pharmaceutical composition of claim 9, which is suitable for pulmonary administration.

14. A method for treating emphysema and associated pulmonary diseases comprising administering to a mammal in need of such therapy a therapeutically effective amount of a compound of claim 1.

* * * * *